US012678101B2

(12) United States Patent (10) Patent No.: US 12,678,101 B2
Drouin et al. (45) Date of Patent: Jul. 14, 2026

(54) METHOD AND APPARATUS FOR DETERMINING THE OPERATIONAL STATE OF A CONTACT DEVICE

(71) Applicant: Bel Devices, Inc., Danville, CA (US)

(72) Inventors: Brent Carson Drouin, San Diego, CA (US); Brent Benbow Nixon, La Quinta, CA (US); Elan Hekier, San Diego, CA (US); Raymond Robert Choye, Belmont, CA (US)

(73) Assignee: Bel Devices, Inc., Danville, CA (US)

( * ) Notice: Subject to any disclaimer, the term of this patent is extended or adjusted under 35 U.S.C. 154(b) by 469 days.

(21) Appl. No.: 17/370,603

(22) Filed: Jul. 8, 2021

(65) Prior Publication Data

US 2022/0008008 A1    Jan. 13, 2022

Related U.S. Application Data

(60) Provisional application No. 63/050,673, filed on Jul. 10, 2020.

(51) Int. Cl.
| | |
|---|---|
| *A61B 7/04* | (2006.01) |
| *A61B 5/00* | (2006.01) |
| *A61B 5/01* | (2006.01) |
| *A61B 7/02* | (2006.01) |
| *G01D 5/14* | (2006.01) |

(Continued)

(52) U.S. Cl.
CPC .............. *A61B 5/6843* (2013.01); *A61B 7/02* (2013.01); *G01D 5/14* (2013.01); *G01J 5/0025* (2013.01); *G01J 5/12* (2013.01); *G01J 5/20* (2013.01); *A61B 2562/0271* (2013.01)

(58) Field of Classification Search
None
See application file for complete search history.

(56) References Cited

U.S. PATENT DOCUMENTS

| | | |
|---|---|---|
| 2007/0085670 A1 | 4/2007 | Peluso |
| 2008/0130706 A1 | 6/2008 | Kellner et al. |

(Continued)

OTHER PUBLICATIONS

Search Report/Written Opinion—Corresponding PCT Application No. PCT/US2021/040885, dated Nov. 23, 2021, 11 pages.

(Continued)

*Primary Examiner* — Tse W Chen
*Assistant Examiner* — Martin Nathan Ortega
(74) *Attorney, Agent, or Firm* — Fish & Richardson P.C.

(57) ABSTRACT

The present invention discloses a method and an analysis apparatus for determining an operational state of a contact device. The method comprising detecting a change in one of temperature and/or proximity data of a contact surface of the contact device with reference to a baseline value. Thereafter, the method comprising generating at least one of temperature profile and proximity profile from the detected change in the at least one of temperature and/or proximity data of the contact surface of the contact device and the baseline value. Lastly, the method comprising comparing the at least one of temperature profile and/or proximity profile with corresponding standard profiles stored in a memory of an analysis apparatus and determining the operational state of the contact device based on the comparison. The contact device may be one of a contact surface, a stethoscope, or a surface monitor.

1 Claim, 7 Drawing Sheets

(51) Int. Cl.
    *G01J 5/00*           (2022.01)
    *G01J 5/12*           (2006.01)
    *G01J 5/20*           (2006.01)

(56)           References Cited

U.S. PATENT DOCUMENTS

| | | | |
|---|---|---|---|
| 2012/0211027 A1* | 8/2012 | Francavilla | C11D 3/0078 |
| | | | 134/113 |
| 2013/0036549 A1 | 2/2013 | Mcklarney | |
| 2016/0066797 A1 | 3/2016 | Lee et al. | |
| 2017/0238812 A1* | 8/2017 | Atlas | A61B 5/747 |
| 2018/0200022 A1* | 7/2018 | Schonfeld | A61L 2/24 |
| 2018/0280555 A1 | 10/2018 | Bilenko et al. | |

OTHER PUBLICATIONS

R. Ellison, "Stethoscope Contamination", N. Engl J. Med. (Jan. 7, 2019).

I.H. Jenkins, B. Monash, J. Wu, et al., The Third Hand: Low rates of stethoscope hygiene on general medicine services. Journal of Hospital Medicine, vol. 10 | No. 7 | Jul. 2015, 457-458.

Knecht et al., "Molecular analysis of bacterial contamination on stethoscopes in an intensive care unit", Infection Control & Hospital Epidemiology (2019), 40, 171-177.

Search Report—corresponding European application No. 21837759. 6, dated Jul. 10, 2024, 8 pages.

* cited by examiner

100

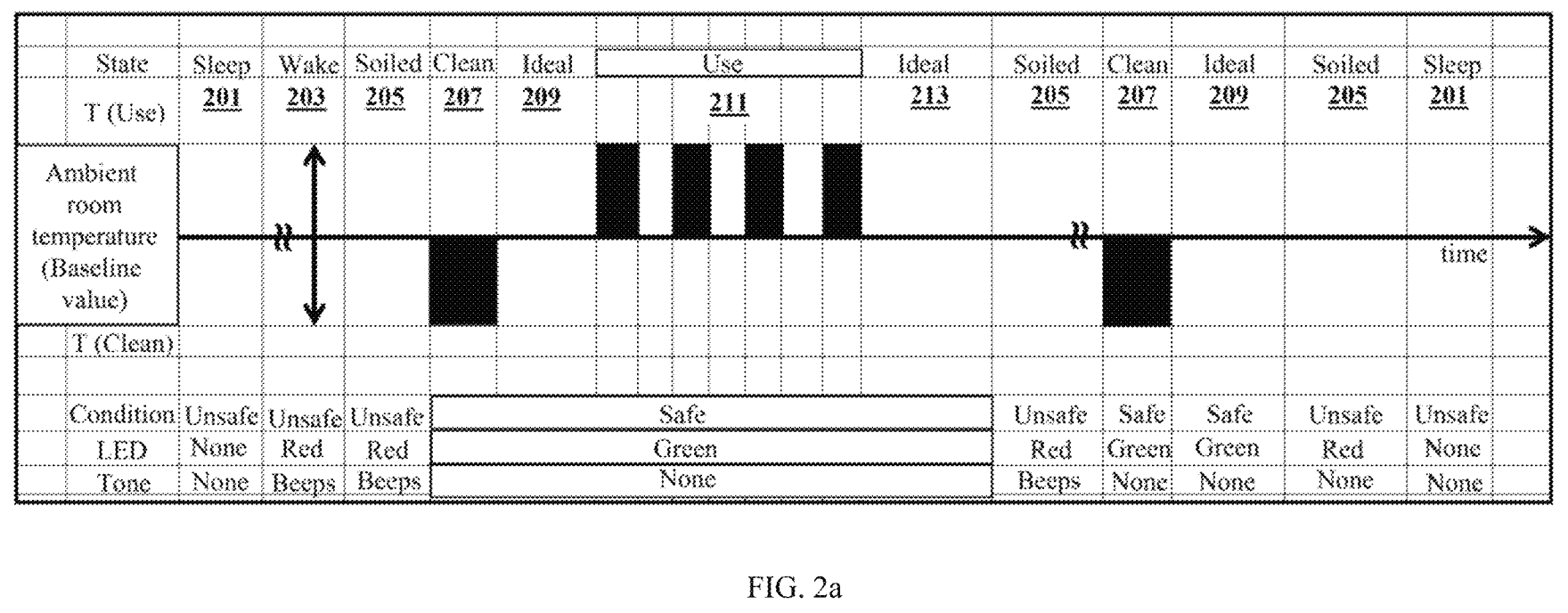

| State | Sleep 201 | Wake 203 | Soiled 205 | Clean 207 | Ideal 209 | Use 211 | Ideal 213 | Soiled 205 | Clean 207 | Ideal 209 | Soiled 205 | Sleep 201 |
|---|---|---|---|---|---|---|---|---|---|---|---|---|
| T (Use) | | | | | | | | | | | | |
| Ambient room temperature (Baseline value) | | | | | | | | | | | | |
| T (Clean) | | | | | | | | | | | | |
| Condition | Unsafe | Unsafe | Unsafe | Safe | | | | Unsafe | Safe | Safe | Unsafe | Unsafe |
| LED | None | Red | Red | Green | | | | Red | Green | Green | Red | None |
| Tone | None | Beeps | Beeps | None | | | | Beeps | None | None | None | None | time

FIG. 2a

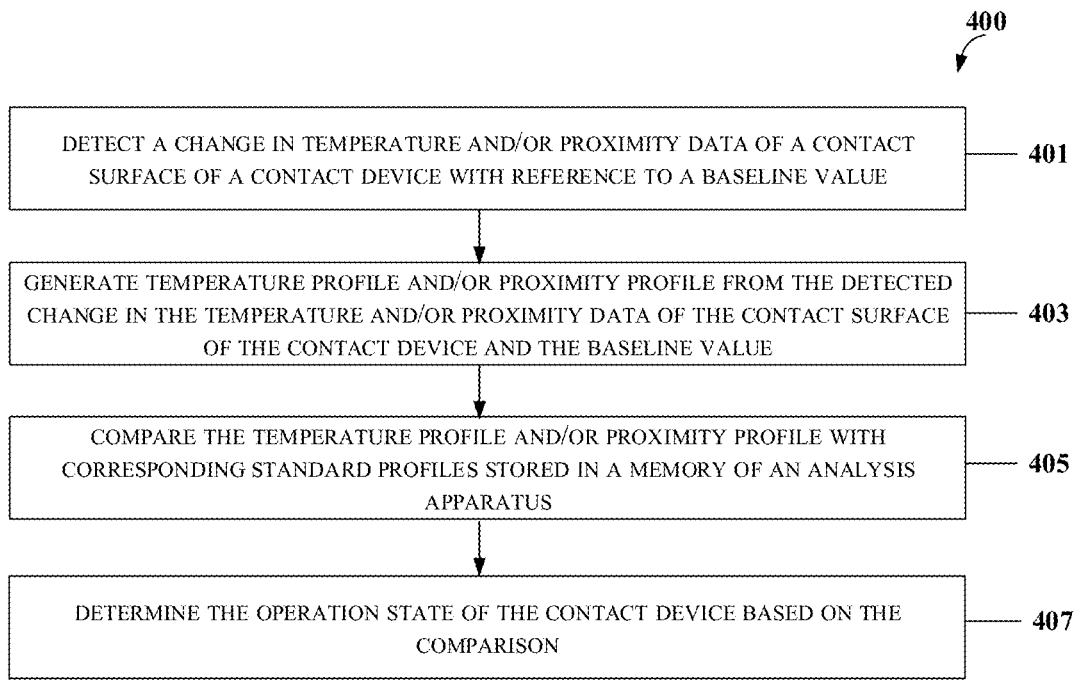

400

DETECT A CHANGE IN TEMPERATURE AND/OR PROXIMITY DATA OF A CONTACT SURFACE OF A CONTACT DEVICE WITH REFERENCE TO A BASELINE VALUE — 401

GENERATE TEMPERATURE PROFILE AND/OR PROXIMITY PROFILE FROM THE DETECTED CHANGE IN THE TEMPERATURE AND/OR PROXIMITY DATA OF THE CONTACT SURFACE OF THE CONTACT DEVICE AND THE BASELINE VALUE — 403

COMPARE THE TEMPERATURE PROFILE AND/OR PROXIMITY PROFILE WITH CORRESPONDING STANDARD PROFILES STORED IN A MEMORY OF AN ANALYSIS APPARATUS — 405

DETERMINE THE OPERATION STATE OF THE CONTACT DEVICE BASED ON THE COMPARISON — 407

FIG. 4

METHOD AND APPARATUS FOR DETERMINING THE OPERATIONAL STATE OF A CONTACT DEVICE

RELATED APPLICATIONS

This application is related to and claims priority to U.S. Provisional Application Ser. No. 63/050,673, filed Jul. 10, 2020, the entire contents of which are herein incorporated by reference.

FIELD OF INVENTION

The present subject matter is generally related to the field of compliance-based cleaning of devices, more particularly, but not exclusively, to a method and an analysis apparatus for determining an operational state of a contact device.

BACKGROUND

Devices, in particular surfaces of the device, that come in contact with the skin of a user, for example a patient, require simple cleaning and disinfection procedures before and after use. The Center for Disease Control and Prevention (CDC) recommends this procedure for non-critical patient care devices such as stethoscopes as well as IV poles. In the commercial sector, this could involve cleaning a surface used by different people in an environment that could spread infection. Though there are typical cleaning recommendations by manufacturers, there is no current method to assess the completion of a cleaning and disinfection procedure after a device has been used.

There are systems that have the ability to identify a unique connected device, clean the device in a designed cleaning station, and log when that device has been put through a cycle at that cleaning station. For instance, U.S. Pat. No. 8,795,438 B2 relates to a stethoscope disinfection monitoring and reporting system structured and configured to track, monitor and report the cleaning, disinfecting, and/or sterilizing of the head portion of a stethoscope. Similarly, U.S. Ser. No. 10/500,016 B2 relates to a method of compliance-based cleaning which includes receiving a piece of equipment to be cleaned in a compliance-based cleaning device, performing a cleaning process on the piece of equipment upon receiving the piece of equipment in the compliance-based cleaning device, monitoring the cleaning process performed on the piece of equipment, and transmitting compliance data from the compliance-based cleaning device to a compliance database.

However, these systems including the above cited prior arts fail to determine the actual use, and subsequent required cleaning after contact with the skin of a patient. Furthermore, there is no real-time indicator that indicates the device is safe for subsequent use.

The information disclosed in this background of the disclosure section is for enhancement of understanding of the general background of the invention and should not be taken as an acknowledgement or any form of suggestion that this information forms the prior art already known to a person skilled in the art.

SUMMARY

In an embodiment, the present disclosure relates to a method for determining an operational state of a contact device. The method includes detecting a change in at least one of temperature and proximity data of a contact surface of the contact device with reference to a baseline value. Thereafter, the method includes generating at least one of temperature profile and proximity profile from the detected change in the at least one of temperature and proximity data of the contact surface of the contact device and the baseline value. Lastly, the method includes comparing the at least one of temperature profile and proximity profile with corresponding standard profiles stored in a memory of an analysis apparatus and determining the operational state of the contact device based on the comparison.

In an embodiment, the present disclosure relates to an analysis apparatus for determining an operational state of a contact device. The analysis apparatus is communicatively coupled to a contact surface of the contact device using at least one of one or more temperature sensors and one or more proximity sensors. The analysis apparatus includes a memory communicatively coupled to the processor, wherein the memory stores standard temperature and/or proximity profiles and processor-executable instructions, which on execution, cause the processor to detect a change in at least one of temperature and proximity data of the contact surface of the contact device with reference to a baseline value. Thereafter, the analysis apparatus is configured to generate at least one of temperature profile and proximity profile from the detected change in the at least one of temperature and proximity data of the contact surface of the contact device and the baseline value. Lastly, the analysis apparatus is configured to compare the at least one of temperature profile and proximity profile with corresponding standard profiles stored in the memory and determine the operational state of the contact device based on the comparison.

In an embodiment, the present disclosure relates to a contact device including an analysis apparatus communicatively coupled to a contact surface of the contact device. The analysis apparatus includes a processor and a memory communicatively coupled to the processor, wherein the memory stores standard temperature and/or proximity profiles and processor-executable instructions, which on execution, cause the processor to detect a change in at least one of temperature and proximity data of the contact surface of the contact device with reference to a baseline value. Thereafter, the analysis apparatus is configured to generate at least one of temperature profile and proximity profile from the detected change in the at least one of temperature and proximity data of the contact surface of the contact device and the baseline value. Lastly, the analysis apparatus is configured to compare the at least one of temperature profile and proximity profile with corresponding standard profiles stored in the memory and determine the operational state of the contact device based on the comparison. The contact device may be one of a stethoscope or a surface monitor.

In an embodiment, the present disclosure relates to a stethoscope including a chestpiece comprising a bell/diaphragm that contacts a surface, a stem connecting the chestpiece and a tubing and at least one analysis apparatus communicatively coupled to the contact surface of the chestpiece. The analysis apparatus includes a processor and a memory communicatively coupled to the processor, wherein the memory stores standard temperature and/or proximity profiles and processor-executable instructions, which on execution, cause the processor to detect a change in at least one of temperature and proximity data of the contact surface of the stethoscope with reference to a baseline value. Thereafter, the analysis apparatus is configured to generate at least one of temperature profile and proximity profile from the detected change in the at least one of temperature and proximity data of the contact surface of the stethoscope and the baseline value. Lastly, the analysis apparatus is configured to compare the at least one of temperature profile and proximity profile with corresponding standard profiles stored in the memory and determine the operational state of the stethoscope based on the comparison. The stethoscope includes at least one indicator arranged at the stem and adjacent to the bell/diaphragm and communicatively coupled to the at least one analysis apparatus for indicating the operational state of the stethoscope.

In an embodiment, the present disclosure relates to a surface monitor including at least one analysis apparatus communicatively coupled to a contact surface of the surface monitor. The analysis apparatus includes a processor and a memory communicatively coupled to the processor, wherein the memory stores standard temperature and proximity profiles and processor-executable instructions, which on execution, cause the processor to detect a change in at least one of temperature and proximity data of the contact surface of the surface monitor with reference to a baseline value. Thereafter, the analysis apparatus is configured to generate at least one of temperature profile and proximity profile from the detected change in the at least one of temperature and proximity data of the contact surface of the surface monitor and the baseline value. Lastly, the analysis apparatus is configured to compare the at least one of temperature profile and proximity profile with corresponding standard profiles stored in the memory and determine the operational state of the surface monitor based on the comparison.

The surface monitor includes at least one indicator arranged on the surface monitor and communicatively coupled to the at least one analysis apparatus for indicating the operational state of the surface monitor. By surface monitor it is meant a grip on a shopping cart, or any other surface that may be gripped by a person, such as, without limitation, a door knob or door handle or a drawer handle or a vehicle steering wheel, etc.

Embodiments of the disclosure according to the above-described method and system may bring about several advantages.

In present disclosure, the method and the analysis apparatus determine the actual use, and subsequent required cleaning after contact with the skin of a patient i.e., determining if a device intended for contact, including skin, has been cleaned prior to use and subsequently cleaned after use. Furthermore, there is real-time indicator that indicates operational state of the contact device. This approach is simple and allows the user of the device to take corrective action in terms of cleaning and disinfection to prevent any spread of infection.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and together with the description, serve to explain the disclosed principles. In the drawings, the digit(s) of a reference number identifies the drawing in which the reference number first appears. The same numbers are used throughout the figures to reference like features and components. Some embodiments of systems and/or methods in accordance with embodiments of the present subject matter are now described below, by way of example only, and with reference to the accompanying figures.

FIG. 2a illustrates a sequence showing a sleep state, a wake state, a use state, a soiled state, a clean state, and idle state of a contact device with respect to time and temperature in accordance with some embodiments of the present disclosure.

FIG. 4 illustrates a flowchart showing a method for determining an operational state of a contact device in accordance with some embodiments of present disclosure.

Figure 1:
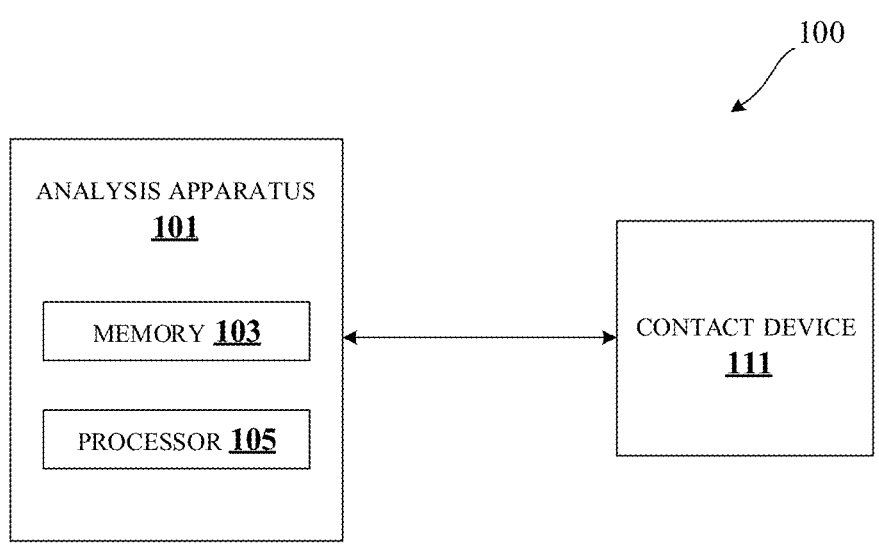
FIG. 1 illustrates an exemplary environment for determining an operational state of a contact device in accordance with some embodiments of the present disclosure.

It should be appreciated by those skilled in the art that any block diagrams herein represent conceptual views of illustrative systems embodying the principles of the present subject matter. Similarly, it will be appreciated that any flowcharts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however, that it is not intended to limit the disclosure to the particular forms disclosed, but on the contrary, the disclosure is to cover all modifications, equivalents, and alternatives falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an exemplary environment for determining an operational state of a contact device in accordance with some embodiments of the present disclosure.

Figure 5A:
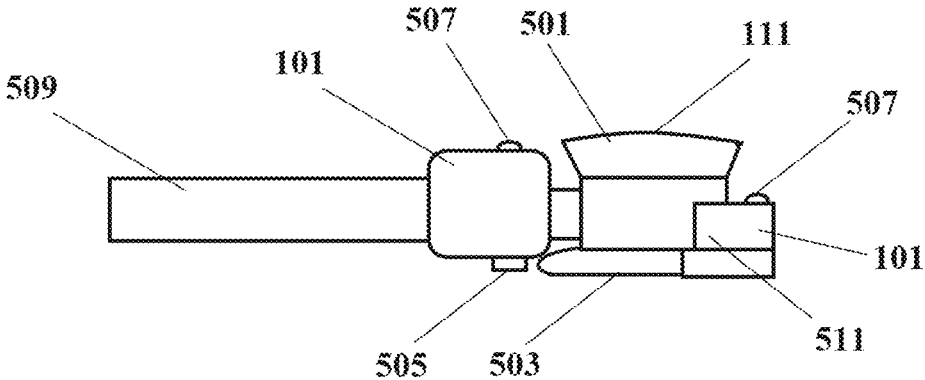
FIGS. 5a and 5b illustrate side view and bottom view, respectively, of a stethoscope embodiment with an analysis apparatus in accordance with some embodiments of the present disclosure.
Figure 5B:
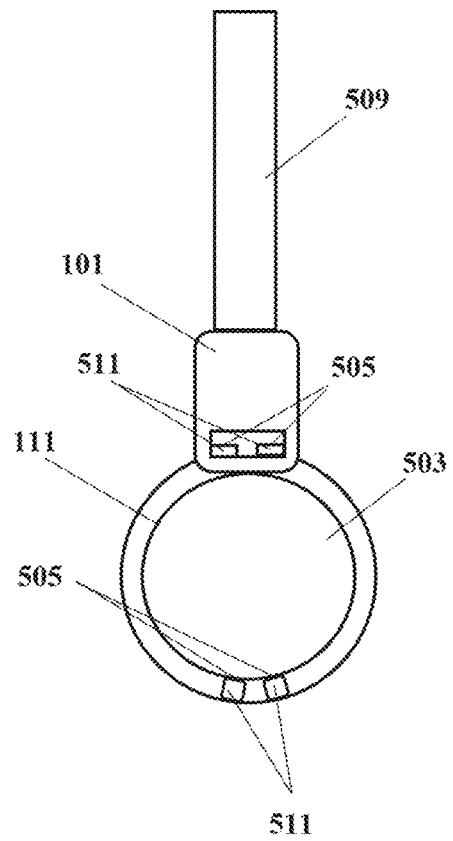
Figure 6A:
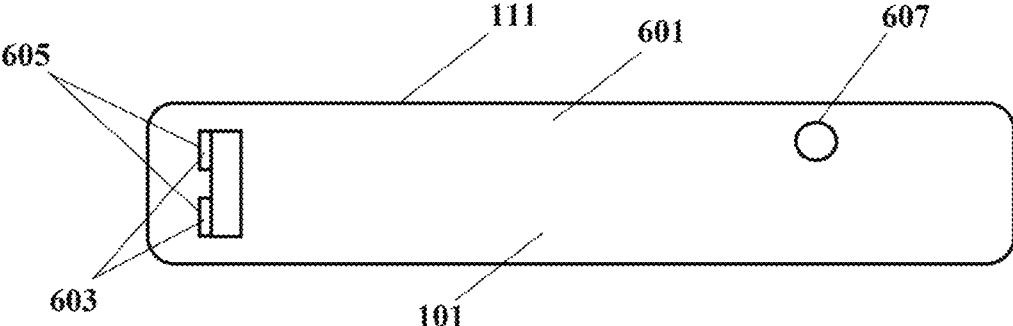
FIG. 6a illustrates top view of a surface monitor embodiment with an analysis apparatus in accordance with some embodiments of the present disclosure.
Figure 6B:
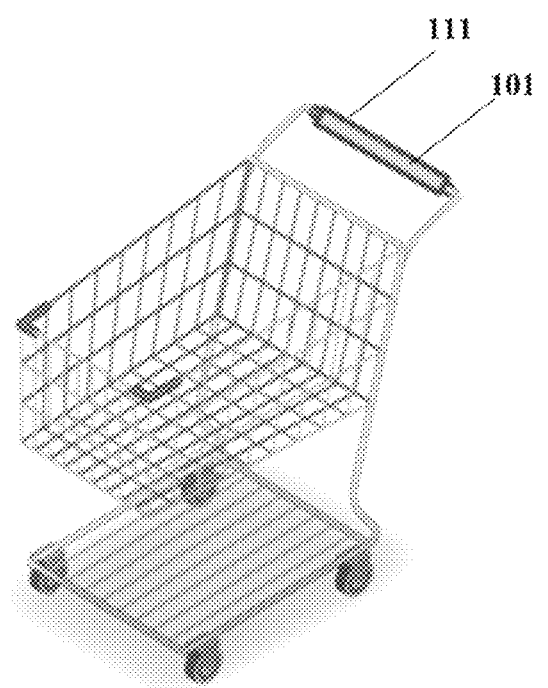
FIG. 6b illustrates an example of implementation of a surface monitor embodiment with an analysis apparatus to a shopping cart in accordance with some embodiments of the present disclosure.

As shown in FIG. 1, the environment 100 includes an analysis apparatus 101 and a contact device 111. The analysis apparatus 101 may be communicatively coupled to a contact surface (not shown in FIG. 1) of the contact device 111 using one or more temperature sensors and/or one or more proximity sensors (not shown in FIG. 1). The proximity sensor may be, without limitation, an impedance-based proximity sensor, a capacitance-based proximity sensor, an infrared-based proximity sensor, or an optical-based proximity sensor. The contact device 111 may refer to any device that is intended for contact including skin of a person. For instance, the contact device 111 may be a chestpiece of a stethoscope, which comprises a contact surface that is placed on a person's skin for listening to the sounds made by the heart, lungs or intestines and the like, as shown in FIGS. 5a and 5b. Here, the analysis apparatus 101 may be communicatively coupled to the contact surface of the chestpiece of the stethoscope using one or more temperature sensors and/or one or more proximity sensors. Similarly, the contact device 111 may be a surface monitor, which comprises a contact surface that is touched frequently by a person's hands, as shown in FIGS. 6a and 6b. Here, the analysis apparatus 101 may be communicatively coupled to the contact surface of the surface monitor using one or more temperature sensors and/or one or more proximity sensors.

In the embodiment of FIG. 1, the analysis apparatus 101 may determine an operational state of the contact device 111 based on detecting a change in temperature and proximity data of the contact surface of the contact device 111 with reference to a baseline value (discussed later in the section). The proximity data may include data related to impedance, capacitance, infrared, or optical. The analysis apparatus 101 may include a memory 103 and a processor 105. The standard temperature profiles and standard proximity profiles may be stored in the memory 103. The memory 103 may be communicatively coupled to the processor 105 of the analysis apparatus 101. The memory 103 may also store processor instructions which may cause the processor 105 to execute the instructions for determining an operational state of the contact device 111. The memory 105 may include, without limitation, memory drives such as solid-state memory devices, solid-state drives and the like.

The processor 105 may include at least one data processor for determining an operational state of the contact device 111. The processor 105 may include specialized processing units such as integrated system (bus) controllers, memory management control units, floating point units, digital signal processing units and the like.

In the embodiment of FIG. 1, the analysis apparatus 101 may be communicatively coupled to at least one of a visual indicator, an audible indicator and a tactile indicator (not shown in FIG. 1) to indicate an operational state of the contact device 111. The visual indicator may include, but not limited to, Light-Emitting Diode (LED) or Liquid Crystal Display (LCD), the audible indicator may include, but not limited to, a tone generator device and the tactile indicator may include, but not limited to, a mechanical vibration device.

In the embodiment of FIG. 1, a battery (not shown in FIG. 1) may be communicatively coupled to the analysis apparatus 101 for powering the operations of the analysis apparatus 101. The battery may be arranged internally or externally to the analysis apparatus 101. The battery may be of a recharging type that is connectable to an external battery charging circuits.

In the same embodiment, the one or more temperature sensors may be of an infrared temperature sensing device type. These sensors are typically, but not limited to, thermistors and thermocouples. In the embodiment, the one or more proximity sensors may allow impedance, capacitance, infrared, or optical measurement. In one embodiment, the one or more proximity sensors may be of a split sensor type providing two electrodes to allow measurement between the electrodes. By sensing proximity data between the two electrodes, a body of a user (or subject) coming in contact with the contact surface of the contact device 111, or the contact surface of the contact device 111 being wiped with cleaning liquid can be determined. The one or more temperature sensors and/or the one or more proximity sensors are positioned on or near the contact surface of the contact device 111 such that the body of a user (or subject) comes in direct contact with the contact surface of the contact device 111.

In the embodiment of FIG. 1, the analysis apparatus 101 may include a known communication apparatus (not shown in FIG. 1) to communicate operational state data wirelessly to an external device (not shown in FIG. 1). The external device may be a computer system, a database, or a cloud server. The operational state data may be used by an administrator or a user of the contact device 111 to perform analysis to improve operating procedure of the analysis apparatus 101 and/or training and compliance of the user of the contact device 111. The wireless communication method/protocols used to communicate the operational state data may include but is not limited to wireless network (for example, using Wireless Application Protocol), Internet, Wi-Fi, Bluetooth and the like.

In the embodiment of FIG. 1, the contact device 111 may comprise analysis apparatus 101, wherein the analysis apparatus 101 is communicatively coupled to a contact surface of the contact device 111. The analysis apparatus 101 may comprise the processor 105 and the memory 103. The memory 103 may be communicatively coupled to the processor 105, wherein the memory 103 may store standard temperature and proximity profiles and processor-executable instructions, which on execution may cause the processor 105 to detect a change in the temperature and/or proximity data of the contact surface of the contact device 111 with reference to a baseline value, generate temperature profile and/or proximity profile from the detected change in the temperature and/or proximity data of the contact surface of the contact device 111 and the baseline value, compare the temperature profile and/or proximity profile with corresponding standard (temperature and/or proximity) profiles stored in the memory 103 and determine the operational state of the contact device 111 based on the comparison. The operational state may comprise: a sleep state, a wake state, a use state, a soiled state, a clean state, and idle state (described below). The contact device 111 may comprise the at least one of the visual indicator, the tone generator device and the mechanical vibration device communicatively coupled to the analysis apparatus 101 for indicating the operational state of the contact device 111. Further, the contact device 111 may comprise one or more temperature sensors coupled to the contact surface of the contact device 111 and/or one or more proximity sensors coupled to the contact surface of the contact device 111, the analysis apparatus 101 being communicatively coupled to the contact surface of the contact device 111 using the one or more temperature sensors and/or the one or more proximity sensors. Furthermore, the analysis apparatus 101 of the contact device 111 may include a communication apparatus to communicate operational state data wirelessly to an external device. The external device may be a computer system, a database, or a cloud server.

In another embodiment, the analysis apparatus 101 may be located externally to the contact device 111. In this situation, the analysis apparatus 101 may receive data from the contact device 111 wirelessly. Based on the received data, the analysis apparatus 101 may detect a change in temperature and/or proximity data of a contact surface of the contact device 111 with reference to a baseline value. Thereafter, the analysis apparatus 101 may generate temperature profile and/or proximity profile from the detected change in the temperature and/or proximity data of the contact surface of the contact device 111 and the baseline value. The analysis apparatus 101 may compare the temperature profile and/or proximity profile with corresponding standard (temperature and/or proximity) profiles stored in the memory 103 of the analysis apparatus 101 and determine the operational state of the contact device 111 based on the comparison. The analysis apparatus 101 may transmit the operational state of the contact device 111 wirelessly to the contact device 111. Subsequently, the contact device 111 may indicate the operational state of the contact device 111 using the at least one of the visual indicator, the tone generator device and the mechanical vibration device. Here, the analysis apparatus 101 may be a mobile device or a computing device. In an embodiment, the analysis apparatus 101 may determine operational state of a plurality of contact devices at a time and transmit the determined operational state to each of the plurality of contact device using unique identifier associated with the contact device.

FIG. 2*a* illustrates a sequence showing a sleep state, a wake state, a use state, a soiled state, a clean state, and idle state of a contact device with respect to time and temperature in accordance with some embodiments of the present disclosure.

Figure 2B:
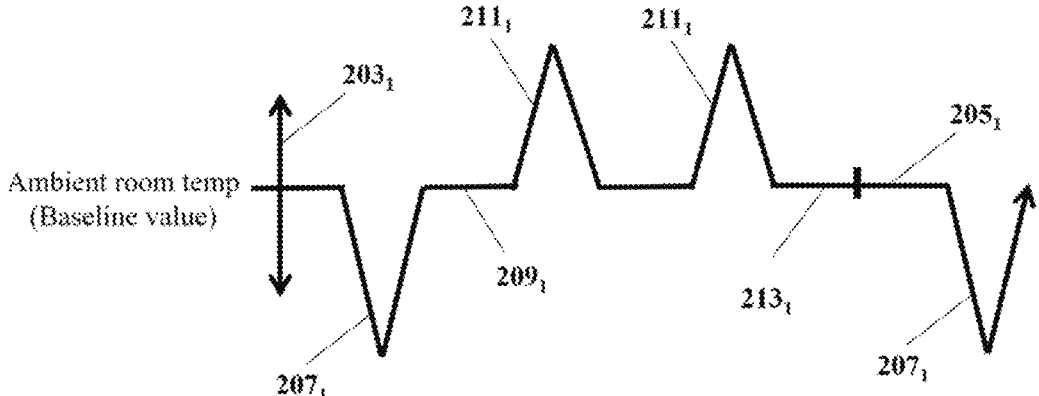
FIG. 2b illustrates a typical temperature sequence characteristics of a contact device in use in accordance with some embodiments of the present disclosure.

The operation of the analysis apparatus 101 for determining an operational state of the contact device 111 is described with reference to FIG. 2*a*. The operational state may comprise a sleep state, a wake state, a use state, a soiled state, a clean state, and idle state. Additionally, there may several idle states during the operation of the contact device 111. The idle states are periods of time where no significant temperature and/or proximity data changes are detected and the contact device 111 is idle at ambient room temperature (baseline value). For sake of simplicity, the operation of the analysis apparatus 101 is explained using temperature sensor. Unique thermal/temperature characteristics are observed when the contact surface of the contact device 111 comes in contact with a body of a user (or subject) or when the contact surface of the contact device 111 is wiped with cleaning liquid. These unique thermal/temperature characteristics of the contact surface of the contact device 111 are illustrated in FIG. 2*b*.

Initially, when the contact device 111 is not in use, the contact device 111 is considered to be in a sleep state 201. During the sleep state 201, the contact device 111 continues to detect/sense an ambient room temperature using one or more temperature sensors and/or one or more proximity sensors coupled to the contact surface of the contact device 111. The ambient room temperature may be considered as a baseline value. In the sleep state 201, a visual indicator, an audible indicator and a tactile indicator are turned off. Thereafter, when the contact surface of the contact device 111 experiences a sharp/predicted deviation i.e., either a sharp/predicted rise or a sharp/predicted fall (or rise) in temperature 2031 from the baseline value, the analysis apparatus 101 detects a change in temperature and/or proximity data of the contact surface of the contact device 111 with reference to the baseline value. The change in the temperature and/or proximity data of the contact surface of the contact device 111 may be when a body of a user (or subject) comes in contact with the contact surface of the contact device 111 or when the contact surface of the contact device 111 is wiped with cleaning liquid. In detail, a sharp/predicted rise in temperature could be when a body of a user (or subject) comes in contact with the contact surface of the contact device 111 and a sharp/predicted fall in temperature could be when the contact surface of the contact device 111 is wiped with cleaning liquid. Thereafter, the analysis apparatus 101 generates temperature profile and/or proximity profile from the detected change in the temperature and/or proximity data of the contact surface of the contact device 111 and the baseline value. The analysis apparatus 101 compares the temperature profile and/or proximity profile with corresponding standard profiles stored in the memory 103 of the analysis apparatus 101 and determine the operational state of the contact device 111 based on the comparison. In this situation, the analysis apparatus 101 determines the operational state of the contact device 111 as a wake state 203 when the comparison indicates a sharp/predicted rise or a sharp/predicted fall in the temperature and/or proximity data of the contact surface of the contact device 111 after no change in the baseline value for a first pre-determined time. The first pre-determined time may be set by a user of the contact device 111 or by an administrator of the analysis apparatus 101. In one embodiment, the contact device 111 may switch from the sleep state 201 to the wake state 203 when the contact device 111 senses movement using an accelerometer, which may be communicatively coupled to the contact device 111. When the contact device 111 is in the wake state 203 from the sleep state 201, the cleanliness of the contact device 111 is unknown and thus, by default, the contact device 111 is assumed to be in a soiled state 205. Consequently, the contact surface of the contact device 111 requires cleaning. The analysis apparatus 101 may indicate the soiled state 205 using at least one of a visual indicator i.e., LED as red, an audible indicator i.e., continuous beep sound and a tactile indicator i.e., continuous vibration. This is an indication to the user of the contact device 111 to clean the contact surface of the contact device 111 prior to use.

When the user wipes/cleans the contact surface of the contact device 111 with cleaning liquid a temperature drop (or a sharp/predicted fall in temperature) 20'71 is observed due to the evaporation of the cleaning liquid. Most liquids used for cleaning purpose undergo a phase change, converting from liquid state to gaseous state, when liquids evaporate. This phase change involves the liquid molecules on the contact surface of the contact device 111 absorbing enough energy from their neighboring liquid molecules to overcome the surrounding vapor pressure. This allows the liquid molecules to change from liquid state to gaseous state taking absorbed energy with them. By taking this absorbed energy away, the remaining liquid on the contact surface of the contact device 111 experiences a lower temperature, called evaporative cooling. In an embodiment, the cleaning liquid may be a water-based cleaning liquid such as a mixture of soap and water, a bleach diluted in water and the like, or an alcohol-based cleaning liquid such as isopropyl, ethanol and the like. When the contact surface of the contact device 111 experiences temperature drop (or a sharp/predicted fall in temperature) from the baseline value, the analysis apparatus 101 detects a change in temperature and/or proximity data of the contact surface of the contact device 111 with reference to the baseline value. Thereafter, the analysis apparatus 101 generates temperature profile and/or proximity profile from the detected change in the temperature and/or proximity data of the contact surface of the contact device 111 and the baseline value. The analysis apparatus 101 compares the temperature profile and/or proximity profile with corresponding standard profiles stored in the memory 103 of the analysis apparatus 101. This comparison of the temperature profile and/or proximity profile with corresponding standard (temperature and/or proximity) profiles allows discriminating from false signals such as other local environmental cooling event like cooling from a room air conditioner unit. In addition to the use of one or more temperature sensors for detecting temperature change, the one or more proximity sensors, also, help discriminate from false signals such as other local environmental cooling event like cooling from a room air conditioner unit. The analysis apparatus 101 determine the operational state of the contact device 111 based on the comparison. In this situation, the analysis apparatus 101 determines the operational state of the contact device 111 as a clean state 207 when the comparison indicates a sharp/predicted fall in the temperature and/or proximity data of the contact surface of the contact device 111. The analysis apparatus 101 may indicate the clean state 207 using at least one of the visual indicator for example, LED as green, an audible indicator for example, no beep sound and a tactile indicator for example, no vibration. This is an indication to the user of the contact device 111 that the contact surface of the contact device 111 is clean and ready to use. After the clean state 207 and before using the contact surface of the contact device 111 for contacting i.e., a use state 211, there may be period referred as an idle state 209 (also, referred as a first idle state) when the contact device 111 is waiting to be used. This is shown as reference 2091 in FIG. 2b.

When the body of the user (or subject) comes in contact with the contact surface of the contact device 111, the analysis apparatus 101 detects a temperature rise (or a sharp/predicted rise in temperature) from the baseline value i.e., the temperature of the contact surface of the contact device 111 undergoes a heating phase during the contact as the body temperature is always higher than ambient room temperature. At this stage, the body of the user (or subject) may come in contact with the contact surface of the contact device 111 repeatedly more than one time during the use of the contact device 111. This is shown as reference 2111 in FIG. 2b, which indicates the body of the user (or subject) coming in contact with the contact surface of the contact device 111 repeatedly and thus, indicating multiple temperature rise and fall cycles. When the contact surface of the contact device 111 experiences temperature rise (or a sharp/predicted rise in temperature) 2111 from the baseline value, the analysis apparatus 101 detects a change in temperature and/or proximity data of the contact surface of the contact device 111 with reference to the baseline value. In this situation, the analysis apparatus 101 determines the operational state of the contact device 111 as a use state 211 when the comparison indicates multiple rise and fall in the temperature and/or proximity data of the contact surface of the contact device 111. Thereafter, the analysis apparatus 101 generates temperature profile and/or proximity profile from the detected change in the temperature and/or proximity data of the contact surface of the contact device 111 and the baseline value. The analysis apparatus 101 compares the temperature profile and/or proximity profile with corresponding standard profiles stored in the memory 103 of the analysis apparatus 101. This comparison of the temperature profile and/or proximity profile with corresponding standard (temperature and/or proximity) profiles allows discriminating from false signals such as other local environmental heating events like room heaters or direct sunlight. In addition to the use of one or more temperature sensors for detecting temperature change, the one or more proximity sensors, also, help discriminate from false signals such as other local environmental heating events like room heaters or direct sunlight. In a situation, when the contact surface of the contact device 111 is exposed to a direct sunlight or to an elevated temperature environment making the contact device 111 unfit for contacting, the analysis apparatus may indicate the soiled state 205 using the visual indicator for example, LED as red. This is an indication to the user of the contact device 111 to clean the contact surface of the contact device 111 prior to next use and also, helps avoid adverse events such as body burns. The analysis apparatus 101 determines the operational state of the contact device 111 based on the comparison. After multiple rise and fall in the temperature and/or proximity data of the contact surface of the contact device 111 i.e., the use state 211, there may be period referred as an idle state 213 (also, referred as a second idle state) when the contact device 111 is not used. This is shown as reference 213₁ in FIG. 2b. In this situation, the analysis apparatus 101 determines the operational state of the contact device 111 as a soiled state 205 when the comparison indicates a sharp/predicted rise in the temperature and/or proximity data of the contact surface of the contact device 111 at a regular interval of time (i.e., the use state 211) and the idle state 213 (i.e., second idle state) has elapsed. The analysis apparatus 101 may indicate the soiled state 205 using at least one of the visual indicator for example, LED as red, an audible indicator for example, continuous beep sound and a tactile indicator for example, continuous vibration. This is an indication to the user of the contact device 111 to clean the contact surface of the contact device 111 prior to next use. The idle state 209 (first idle state) and the idle state 213 (second idle state) may be of same idle time duration or of different idle time duration.

When the user wipes/cleans the contact surface of the contact device 111, the analysis apparatus 101 repeats the steps described above and determines the operational state of the contact device 111 as the clean state 207. The analysis apparatus 101 may indicate the clean state 207 using at least one of the visual indicator for example, LED as green, an audible indicator for example, no beep sound and a tactile indicator for example, no vibration. This is an indication to the user of the contact device 111 that the contact surface of the contact device 111 is clean and ready to use.

Thereafter, when the contact device 111 is not used for a second pre-determined time, the analysis apparatus 101 detects no change in temperature and/or proximity data of a contact surface of a contact device with reference to a baseline value. Thereafter, the analysis apparatus 101 generates temperature profile and/or proximity profile using unchanged temperature and/or proximity data of the contact surface of the contact device 111 and the baseline value. The analysis apparatus 101 compares the temperature profile and/or proximity profile with corresponding standard profiles stored in the memory 103 of the analysis apparatus 101 and determines the operational state of the contact device 111 based on the comparison. In this situation, the analysis apparatus 101 determines the operational state of the contact device 111 as a soiled state 205 when the comparison indicates no change in the baseline value for a second pre-determined time after a sharp/predicted fall in the temperature and/or proximity data of the contact surface of the contact device 111. The second pre-determined time may be set by the user of the contact device 111 or by the administrator of the analysis apparatus 101. The analysis apparatus 101 may indicate the soiled state 205 using at least one of the visual indicator for example, LED as red, an audible indicator for example, no beep sound and a tactile indicator for example, no vibration. This is an indication to the user of the contact device 111 to clean the contact surface of the contact device 111 prior to next use.

Subsequently, when the contact device 111 is not used, the contact device 111 is considered to be in a sleep state 201. During the sleep state 201, the contact device 111 continues to detect/sense an ambient room temperature using the one or more temperature sensors and/or one or more proximity sensors coupled to the contact surface of the contact device 111.

Figure 3:
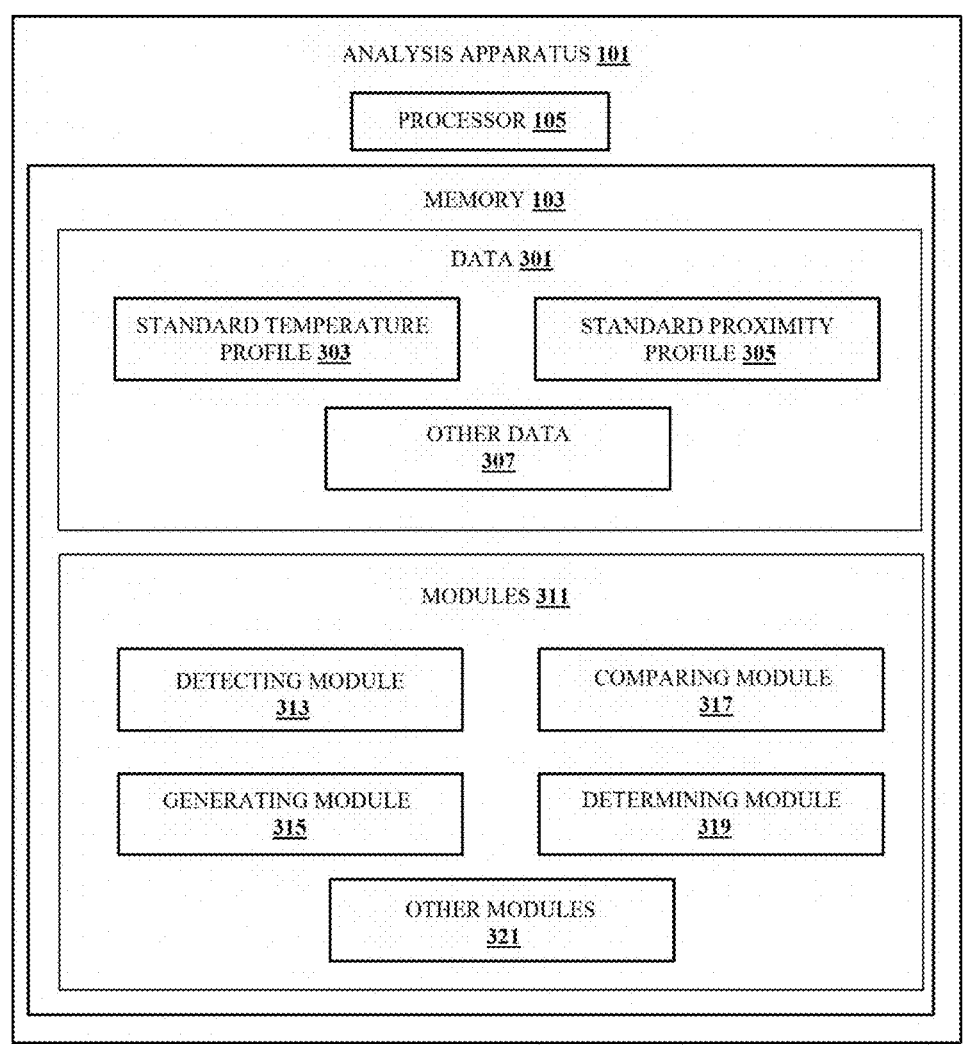
FIG. 3 shows a block diagram of an analysis apparatus in accordance with some embodiments of the present disclosure.

FIG. 3 shows a block diagram of an analysis apparatus in accordance with some embodiments of the present disclosure.

The analysis apparatus 101, in addition to the memory 103 and the processor 105 described in FIG. 1, may include data 301 and one or more modules 311, which are described herein in detail. In the embodiment, the data 301 may be stored within the memory 103. The data 301 may include, for example, standard temperature profile 303, standard proximity profile 305 and other data 307. The analysis apparatus 101 may, also, be referred as an analysis electronics.

The standard temperature profile 303 may include at least one standard temperature profile that are used for comparing with temperature profile generated by the analysis apparatus 101. The at least one standard temperature profile may be stored in the standard temperature profile 303 by a user of the contact device 111 or by an administrator of the analysis apparatus 101.

The standard proximity profile 305 may include at least one standard impedance profile, standard capacitance profile, standard infrared profile and standard optical profile that are used for comparing with proximity profile generated by the analysis apparatus 101. The at least one standard impedance profile, standard capacitance profile, standard infrared profile and standard optical profile may be stored in the standard proximity profile 305 by the user of the contact device 111 or by the administrator of the analysis apparatus 101.

The other data 307 may store data, including temporary data and temporary files, generated by one or more modules 311 for performing the various functions of the analysis apparatus 101.

In the embodiment, the data 301 in the memory 103 are processed by the one or more modules 311 present within the memory 103 of the analysis apparatus 101. In the embodiment, the one or more modules 311 may be implemented as dedicated hardware units. As used herein, the term module refers to an Application Specific Integrated Circuit (ASIC), an electronic circuit, a Field-Programmable Gate Arrays (FPGA), Programmable System-on-Chip (PSoC), a combinational logic circuit, and/or other suitable components that provide the described functionality. In some implementations, the one or more modules 311 may be communicatively coupled to the processor 105 for performing one or more functions of the analysis apparatus 101. The said modules 311 when configured with the functionality defined in the present disclosure will result in a novel hardware.

In one implementation, the one or more modules 311 may include, but are not limited to, a detecting module 313, a generating module 315, a comparing module 317, and a determining module 319. The one or more modules 311 may, also, include other modules 321 to perform various miscellaneous functionalities of the analysis apparatus 101.

The detecting module 313 may detect a change in temperature and/or proximity data of a contact surface of the contact device 111 with reference to a baseline value. The proximity data may include data related to impedance, capacitance, infrared, or optical. The change in temperature and/or proximity data of the contact surface of the contact device 111 may be detected when a body of a user (or subject) comes in contact with the contact surface of the contact device 111 or when the contact surface of the contact device 111 is wiped with cleaning liquid.

The generating module 315 may generate temperature profile and/or proximity profile from the detected change, detected by the detecting module 313, in the temperature and/or proximity data of the contact surface of the contact device 111 and the baseline value.

The comparing module 317 may compare the temperature profile and/or proximity profile, generated by the generating module 315, with corresponding standard profiles stored in the memory 103 i.e., in the standard temperature profile 303 and the standard proximity profile 305 of the analysis apparatus 101.

The determining module 319 may determine the operational state of the contact device 111 based on the comparison received from the comparing module 317. The operational state of the contact device 111 may be indicated using at least one of a visual indication, an audible indication and a tactile indication. The operational state may comprise the sleep state 201, the wake state 203, the soiled state 205, the clean state 207, the idle state 209 (i.e., first idle state) and the use state 211. The determining the operational state of the contact device 111 based on the comparison may comprise:

determining the operational state of the contact device 111 as the wake state 203 when the comparison indicates a sharp/predicted rise or a sharp/predicted fall in the temperature and/or proximity data of the contact surface of the contact device 111 after no change in the baseline value for a first pre-determined time.

determining the operational state of the contact device as the soiled state when the comparison indicates no change in the baseline value after a sharp/predicted fall in the temperature and/or proximity data of the contact surface of the contact device and the first idle state 209 has elapsed, or determining the operational state of the contact device 111 as the soiled state 205 when the comparison indicates a sharp/predicted rise in the temperature and/or proximity data of the contact surface of the contact device 111 at a regular interval of time and a second idle state 213 has elapsed.

determining the operational state of the contact device 111 as the clean state 207 when the comparison indicates a sharp/predicted fall in the temperature and/or proximity data of the contact surface of the contact device 111.

determining the operational state of the contact device as
the use state 211 when the comparison indicates a
sharp/predicted rise in the temperature and/or proxim-
ity data of the contact surface of the contact device at
a regular interval of time.

FIG. 4 illustrates a flowchart showing a method for
determining an operational state of a contact device in
accordance with some embodiments of present disclosure.

As illustrated in FIG. 4, the method 400 includes one or
more blocks for determining an operational state of the
contact device 111. The method 400 may be described in the
general context of computer executable instructions. Gen-
erally, computer executable instructions can include rou-
tines, programs, objects, components, data structures, pro-
cedures, modules, and functions, which perform particular
functions or implement particular abstract data types.

The order in which the method 400 is described is not
intended to be construed as a limitation, and any number of
the described method blocks can be combined in any order
to implement the method. Additionally, individual blocks
may be deleted from the methods without departing from the
scope of the subject matter described herein. Furthermore,
the method can be implemented in any suitable hardware,
software, firmware, or combination thereof.

At block 401, the detecting module 313 may detect a
change in temperature and/or proximity data of a contact
surface of the contact device 111 with reference to a baseline
value. The change in temperature and/or proximity data of
the contact surface of the contact device 111 may be detected
when a body of a user (or subject) comes in contact with the
contact surface of the contact device 111 or when the contact
surface of the contact device 111 is wiped with cleaning
liquid.

At block 403, the generating module 315 may generate
temperature profile and/or proximity profile from the
detected change in the temperature and/or proximity data of
the contact surface of the contact device 111 and the baseline
value.

At block 405, the comparing module 317 may compare
the temperature profile and/or proximity profile with corre-
sponding standard profiles stored in the memory 103 of the
analysis apparatus 101.

At block 407, the determining module 319 may determine
the operational state of the contact device 111 based on the
comparison. The operational state of the contact device 111
may be indicated using at least one of a visual indication, an
audible indication and a tactile indication. The operational
state may comprise a sleep state 201, a wake state 203, a
soiled state 205, a clean state 207, an idle state 209 (i.e., first
idle state) and a use state 211. The determining the opera-
tional state of the contact device 111 based on the compari-
son may comprise:

determining the operational state of the contact device 111
as a wake state 203 when the comparison indicates a
sharp/predicted rise or a sharp/predicted fall in the
temperature and/or proximity data of the contact sur-
face of the contact device 111 after no change in the
baseline value for a first pre-determined time.

determining the operational state of the contact device 111
as a soiled state 205 when the comparison indicates no
change in the baseline value after a sharp/predicted fall
in the temperature and/or proximity data of the contact
surface of the contact device 111 and the first idle state
209 has elapsed, or determining the operational state of
the contact device 111 as a soiled state 205 when the
comparison indicates a sharp/predicted rise in the tem-
perature and/or proximity data of the contact surface of the contact device 111 at a regular interval of time and
a second idle state 213 has elapsed.

determining the operational state of the contact device 111
as a clean state 207 when the comparison indicates a
sharp/predicted fall in the temperature and/or proximity
data of the contact surface of the contact device 111.

determining the operational state of the contact device 111
as a use state 211 when the comparison indicates a
sharp/predicted rise in the temperature and/or proxim-
ity data of the contact surface of the contact device 111
at a regular interval of time.

FIGS. 5a and 5b illustrate side view and bottom view,
respectively, of a stethoscope embodiment with an analysis
apparatus in accordance with some embodiments of the
present disclosure.

In the stethoscope embodiment, the stethoscope may
comprise a chestpiece (also, referred as the contact device
111) that includes a bell 501 and a diaphragm (i.e., contact
surface) 503. A stem (not shown in FIGS. 5a and 5b) may
connect the chestpiece i.e., the contact device 111 and a
tubing 509. The stethoscope may comprise one or more
temperature sensors 505 arranged proximal to the diaphragm
503 of the chestpiece i.e., the contact device 111 and the
stem and/or one or more proximity sensors 511 arranged
adjacent, or concurrent, to the one or more temperature
sensors 505. The stethoscope may comprise at least one
analysis apparatus 101 communicatively coupled to the
diaphragm 503 of the chestpiece i.e., the contact device 111
using the one or more temperature sensors 505 and/or the
one or more proximity sensors 511. The components of
analysis apparatus 101 are same as the components of the
analysis apparatus 101 described with reference to FIG. 3
and the operation of the analysis apparatus 101 for deter-
mining an operational state of the stethoscope is same as
described with reference to FIGS. 2a and 2b. The opera-
tional state may comprise the sleep state 201, the wake state
203, the soiled state 205, the clean state 207, the idle state
209 (i.e., first idle state) and the use state 211. The stetho-
scope may comprise at least one indicator arranged at the
stem and adjacent to the bell 501 and/or diaphragm 503 and
communicatively coupled to the at least one analysis appa-
ratus 101 for indicating the operational state of the stetho-
scope. The indicator may be at least one of a visual indicator
507, a tone generator device and a mechanical vibration
device. Furthermore, the analysis apparatus 101 of the
stethoscope may include a communication apparatus to
communicate operational state data wirelessly to an external
device. The external device may be a computer system, a
database, or a cloud server. The communication apparatus
may be attached to the tubing 509 of the stethoscope.

In brief, the operation of the stethoscope embodiment is
explained here. Initially, when the chestpiece i.e., the contact
device 111 of the stethoscope is not in use, the chestpiece is
considered to be in the sleep state 201. Upon waking i.e., the
wake state 203, the cleanliness of the chestpiece of the
stethoscope is unknown and thus, by default, the chestpiece
is assumed to be in the soiled state 205. The analysis
apparatus 101 indicates the soiled state 205 using the visual
indicator for example, LED as red until the chestpiece is
cleaned. Once a cleaning sequence is detected i.e., the clean
state 207, the analysis apparatus 101 indicates the clean state
207 using the visual indicator for example, LED as green.
This is an indication to the user that the chestpiece of the
stethoscope is ready for auscultation. When the auscultation
is initiated i.e., the use state 211 after an idle state 209 (i.e.,
first idle state), the analysis apparatus 101 detects multiple
temperature rise and fall cycles. After auscultation, there may be a period i.e., the idle state 213 (i.e., second idle state) when the chestpiece is not used. If the chestpiece is not used by the end of the idle state 213 (i.e., second idle state), the analysis apparatus 101 indicates the soiled state 205 using the visual indicator for example, LED as red. This is an indication to the user to clean the bell 501 and diaphragm 503 of the chestpiece prior to next use i.e., fresh auscultation. If the chestpiece was cleaned, but no auscultations initiated, and a short idle time expired i.e., the idle time/state 209 (i.e., first idle state), the analysis apparatus 101 changes to the soiled state 205 and indicates the soiled state 205 using the visual indicator for example, LED as red. Thereafter, with no auscultations initiated, the analysis apparatus 101 changes to the sleep state 201 with the indicators turned off.

The implementation of the analysis apparatus 111 is not limited to the chestpiece i.e., the contact device 111 of the stethoscope but can be implemented on any surface that experiences contact or touch with a body of a user (or subject) and requires cleaning to prevent spread of infection, for example, any diagnostic devices such ophthalmic slit lamps, Optical Coherence Tomography (OCT) imaging devices, visual field measurement devices and the like.

FIG. 6a illustrates top view of a surface monitor embodiment with an analysis apparatus in accordance with some embodiments of the present disclosure.

In the surface monitor embodiment, the surface monitor may also be referred as the contact device 111 that includes a contact surface 601. The surface monitor may comprise one or more temperature sensors 603 arranged proximal to the contact surface 601 of the surface monitor i.e., the contact device 111 and/or one or more proximity sensors 605 arranged adjacent to the one or more temperature sensors 603. The surface monitor i.e., the contact device 111 may comprise at least one analysis apparatus 101 communicatively coupled to the contact surface 601 of the surface monitor i.e., the contact device 111 using the one or more temperature sensors 603 and/or the one or more proximity sensors 605. The components of analysis apparatus 101 are same as the components of the analysis apparatus 101 described with reference to FIG. 3 and the operation of the analysis apparatus 101 for determining an operational state of the surface monitor is same as described with reference to FIGS. 2a and 2b. The operational state may comprise the sleep state 201, the wake state 203, the soiled state 205, the clean state 207, the idle state 209 (i.e., first idle state) and the use state 211. The surface monitor i.e., the contact device 111 may comprise at least one indicator arranged on the surface monitor and communicatively coupled to the at least one analysis apparatus 101 for indicating the operational state of the surface monitor. The indicator may be at least one of a visual indicator 607, a tone generator device and a mechanical vibration device. Furthermore, the analysis apparatus 101 of the surface monitor may include a communication apparatus to communicate operational state data wirelessly to an external device. The external device may be a computer system, a database, or a cloud server.

In brief, the operation of the surface monitor embodiment is explained here. Initially, when the surface monitor i.e., the contact device 111 is not in use, the surface monitor is considered to be in the sleep state 201. Upon waking i.e., the wake state 203, the cleanliness of the surface monitor is unknown and thus, by default, the surface monitor is assumed to be in the soiled state 205. The analysis apparatus 101 indicates the soiled state 205 using the visual indicator for example, LED as red until the surface monitor is cleaned. Once a cleaning sequence is detected i.e., the clean state 207, the analysis apparatus 101 indicates the clean state 207 using the visual indicator for example, LED as green. This is an indication to the user that the surface monitor is ready for use. There may be period referred as an idle state 209 before the surface monitor is contacted. When the surface monitor is contacted repeatedly i.e., the use state 211, the analysis apparatus 101 detects multiple temperature rise and fall cycles. After using the surface monitor, there may be a period i.e., the idle state 213 (i.e., second idle state) when the surface monitor is not used. If the surface monitor is not used by the end of the idle state 213 (i.e., second idle state), the analysis apparatus 101 indicates the soiled state 205 using the visual indicator for example, LED as red. This is an indication to the user to clean the contact surface 601 of the surface monitor prior to next use. If the surface monitor was cleaned i.e., the clean state 207, but no contacts initiated, and a short idle time expired i.e., the idle time/state 209 (i.e., first idle state), the analysis apparatus 101 changes to the soiled state 205 and indicates the soiled state 205 using the visual indicator for example, LED as red. Thereafter, with no contacts initiated, the analysis apparatus 101 changes to the sleep state 201 with the indicators turned off.

An implementation of the surface monitor (i.e., the contact device 111) embodiment with the analysis apparatus 101 to a handle of a shopping cart is shown in FIG. 6b. The surface monitor including the analysis apparatus 101 may be attached to the handle of the (shopping) cart by means of an adhesive backing/adhesive sticker. The implementation of the surface monitor is not limited to a handle of a shopping cart as the surface monitor embodiment can be implemented on any other surface that may be gripped by a person, such as, without limitation, a handle of a basket, a door knob, a door handle, a drawer handle, a vehicle steering wheel, a handle of a gymnasium equipment and the like.

Some of the technical advantages of the present disclosure are listed below.

In present disclosure, the method and the analysis apparatus determine the actual use, and subsequent required cleaning after contact with the skin of a patient i.e., determining if a device intended for contact, including skin, has been cleaned prior to use and subsequently cleaned after use. Furthermore, there is real-time indicator that indicates operational state of the contact device. This approach is simple and allows the user of the device to take corrective action in terms of cleaning and disinfection to prevent any spread of infection.

One or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media include all computer-readable media except for a transitory. The code implementing the described operations may further be implemented in hardware logic (e.g., an integrated circuit chip, Programmable Gate Array (PGA), Application Specific Integrated Circuit (ASIC), etc.).

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4 show certain events occurring in a certain order. In alternative embodiments, certain operations may be performed in a different order, modified or removed. Moreover, steps may be added to the above-described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference number | Description |
| --- | --- |
| 100 | Environment |
| 101 | Analysis apparatus |
| 103 | Memory |
| 105 | Processor |
| 111 | Contact device |
| 201 | Sleep state |
| 203 | Wake state |
| 205 | Soiled state |
| 207 | Clean state |
| 209 | First Idle state |
| 211 | Use state |
| 213 | Second idle state |
| 301 | Data |
| 303 | Standard temperature profile |
| 305 | Standard proximity profile |
| 307 | Other data |
| 311 | Modules |
| 313 | Detecting module |
| 315 | Generating module |
| 317 | Comparing module |
| 319 | Determining module |
| 321 | Other modules |
| 501 | Bell |
| 503 | Diaphragm |
| 505, 603 | Temperature sensors |
| 507, 607 | Visual indicators |
| 509 | Tubing |
| 511, 605 | Proximity sensors |
| 601 | Surface monitor |

What is claimed is:

1. A stethoscope having an indication of clean status comprising:

a contact surface on the stethoscope being configured to contact a body surface;

one or more temperature sensors mounted on the contact surface of the stethoscope, and being configured to detect a change of temperature;

an analysis apparatus communicatively coupled to the one or more temperature sensors, and a display, the analysis apparatus comprising: a processor, and a memory communicatively coupled to the processor, wherein the memory stores a plurality of predetermined standard profiles of a series of temperature changes in a predetermined time based on a phase change of a cleaning solution on a contact surface of the stethoscope and processor-executable instructions, which on execution, cause the processor to:

determine a baseline value of temperature for an environment of the stethoscope;

store the baseline value of temperature for the environment;

detect, by the one or more temperature sensors, a series of temperature changes in a predetermined time on data of the contact surface of the stethoscope;

analyze the series of temperature changes detected;

determine a temperature profile with a corresponding standard profiles stored in the memory;

determine the clean status of the stethoscope as a clean state when a match exists between the temperature profile and one of the plurality of a corresponding standard profile;

display, by at least one visual indicator on the display, a clean status as a clean state of the stethoscope and is ready for use, wherein use of the stethoscope will prevent the spread of infection:

detect, by the one or more temperature sensors, the temperature of the environment has returned to the baseline value:

further detect, by the one or more temperature sensors, a temperature of the contact surface has changed from the baseline value indicative of the stethoscope in use and not clean; and activate, the at least one visual indicator to indicate the clean status as an unclean state of the stethoscope.

* * * * *